US009902957B2

(12) United States Patent
Cooley et al.

(10) Patent No.: US 9,902,957 B2
(45) Date of Patent: Feb. 27, 2018

(54) AMPHIPATHIC CO-OLIGOMERS FOR THE DELIVERY OF SIRNA

(75) Inventors: Christina Barnes Cooley, San Diego, CA (US); Erika Geihe Stanzl, Stanford, CA (US); Robert M. Waymouth, Stanford, CA (US); Paul Wender, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 203 days.

(21) Appl. No.: 14/342,480

(22) PCT Filed: Sep. 5, 2012

(86) PCT No.: PCT/US2012/053797
§ 371 (c)(1),
(2), (4) Date: Jul. 8, 2014

(87) PCT Pub. No.: WO2013/036532
PCT Pub. Date: Mar. 14, 2013

(65) Prior Publication Data
US 2014/0350077 A1    Nov. 27, 2014

Related U.S. Application Data

(60) Provisional application No. 61/531,495, filed on Sep. 6, 2011.

(51) Int. Cl.
| *C12N 15/113* | (2010.01) |
| *A01N 37/12* | (2006.01) |
| *A01N 37/44* | (2006.01) |
| *A61K 9/127* | (2006.01) |
| *A61K 9/00* | (2006.01) |
| *A61K 47/59* | (2017.01) |

(52) U.S. Cl.
CPC .......... *C12N 15/113* (2013.01); *A61K 9/0019* (2013.01); *A61K 47/593* (2017.08); *C12N 2310/14* (2013.01); *C12N 2320/32* (2013.01)

(58) Field of Classification Search
CPC .............. C12N 15/113; C12N 2310/14; C12N 2320/32; A61K 47/593; A61K 9/0019
See application file for complete search history.

(56) References Cited

U.S. PATENT DOCUMENTS

| 7,169,814 B2 | 1/2007 | Rothbard et al. |
| 2010/0015050 A1* | 1/2010 | Panyam ........... A61K 47/48107 514/1.1 |

OTHER PUBLICATIONS

Kim et al. (Biomaterials, pp. 5505-5514, available online May 6, 2011).*
Cooley; et al., "Oligocarbonate Molecular Transporters: Oligomerization-Based Syntheses and Cell-Penetrating Studies", J. Am. Chem. Soc. (Oct. 2009), 131:16401-3.

* cited by examiner

*Primary Examiner* — Alma Pipic
(74) *Attorney, Agent, or Firm* — Glenn J. Foulds; Bozicevic, Field & Francis LLP

(57) ABSTRACT

Co-oligomer compounds, complexes of the same with polyanions, such as siRNAs, and methods for using the same are provided. the delivery of polynucleotides, into a cell. The subject co-oligomers include at least a liphopilic monomer and at least a hydrophilic monomer (e.g., a guanidinium containing monomer). In some embodiments, the co-oligomer compounds are capable of complexing a siRNA of interest, thereby increasing the cell permeability of the siRNA, prior to release of the siRNA into the cell. In some embodiments, the subject method is a method of delivery a siRNA into a cell. In some embodiments, the subject method is a method of reducing expression of a protein target of a siRNA of interest. The subject co-oligomer/siRNA complexes may be formulated and administered to a subject to treat a condition resulting from expression of a protein target of the siRNA of interest.

33 Claims, 4 Drawing Sheets

AMPHIPATHIC CO-OLIGOMERS FOR THE DELIVERY OF SIRNA

GOVERNMENT RIGHTS

This invention was made with Government support under contract 0957386 awarded by the National Science Foundation and under contracts CA031841 and CA031845 awarded by the National Institutes of Health. The Government has certain rights in this invention.

BACKGROUND

Since the discovery of RNA interference (RNAi), first in plants in 1990 and then in animals in 1998, this pathway has generated significant interest for its utility in biological studies as well as in drug development. As part of the RNAi pathway, small interfering RNAs (siRNAs) induce post-transcriptional gene silencing in a sequence-specific manner utilizing endogenous cellular machinery, in essence suppressing protein synthesis and thus effectively inhibiting protein function. This technology is used routinely as a research tool for target validation, biological pathway analysis, and imaging of biological systems. In addition, the ubiquity of the RNAi pathway within the body and the ease with which the target of interest can be altered have made siRNA an attractive class of molecules for the treatment of cancer, viral and bacterial infections, neurodegenerative diseases, and genetic disorders. In addition, RNAi therapies are of interest to enhance the effectiveness of existing therapies; for example, RNAi could be used to target multidrug resistance genes to re-sensitize cancer cells to traditional chemotherapy.

SiRNA is subject to rapid enzymatic degradation and has difficulty entering the cell due to its relatively large size and polyanionic polar nature that resists passage across the non-polar membrane of a cell. These difficulties suggest that delivery of siRNA into cells and tissue within the body is a challenge to the realization of siRNA for diagnostic, imaging and therapeutic use. Delivery systems that both prevent enzymatic degradation and effectively deliver siRNA across the cell membrane are of interest for the utility of biological siRNA tools and siRNA therapies to be realized.

SUMMARY OF THE DISCLOSURE

Co-oligomer compounds, complexes of the same with polyanions, such as siRNAs, and methods for using the same are provided for the delivery of polynucleotides, into a cell. The subject co-oligomers include at least a liphopilic monomer and at least a hydrophilic monomer (e.g., a guanidinium containing monomer). In some embodiments, the co-oligomer compounds are capable of complexing a siRNA of interest, thereby increasing the cell permeability of the siRNA, prior to release of the siRNA inside the cell. In some embodiments, the subject method is a method of delivering a siRNA into a cell.

In some embodiments, a method is provided for reducing expression of a target protein or proteins. The subject co-oligomer/siRNA complexes may be formulated and administered to a subject to treat a condition resulting from expression of a protein or proteins.

These and other advantages, and features of the disclosure will become apparent to those persons skilled in the art upon reading the details of the compositions and methods of use more fully described below.

DEFINITIONS

Figure 1:
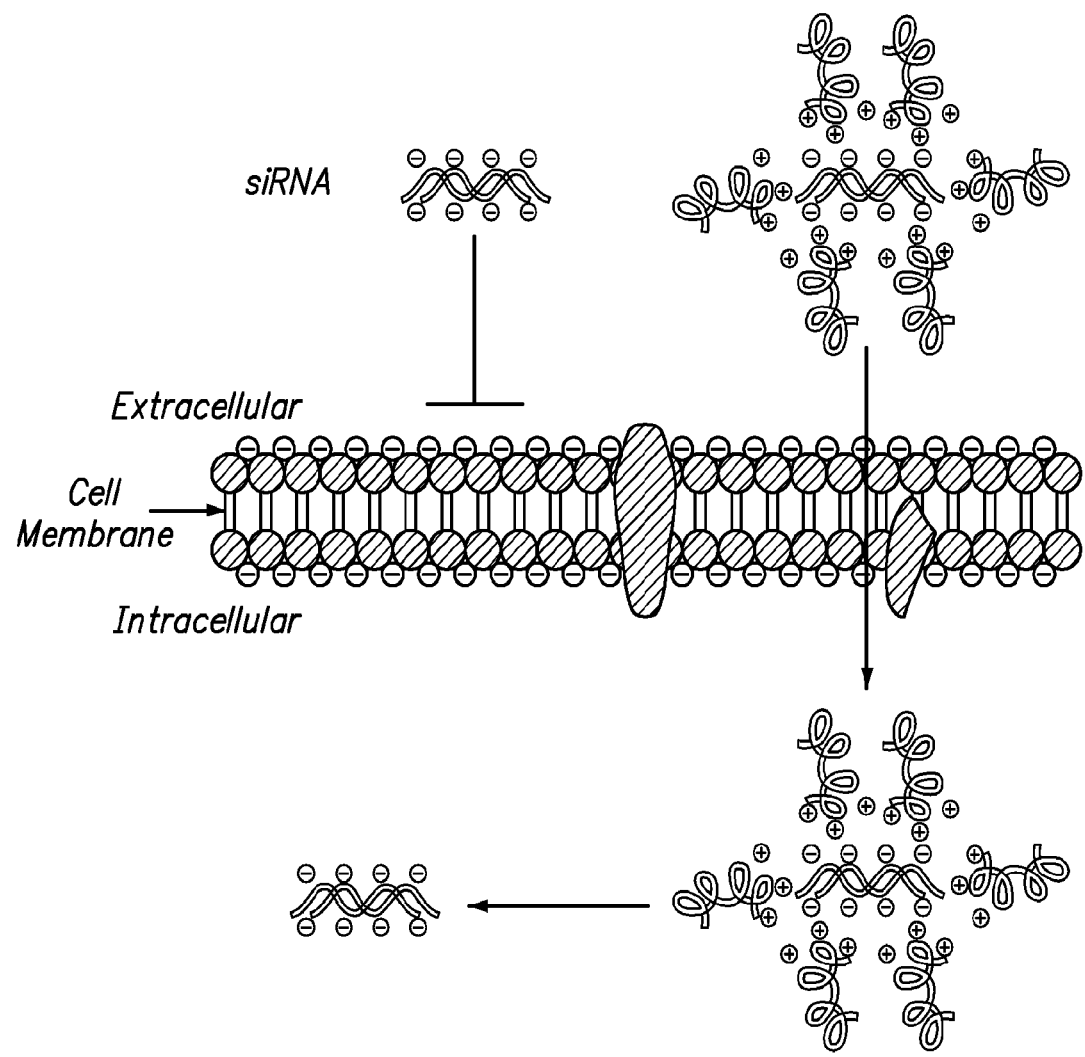
FIG. 1 illustrates the complexing and delivery of siRNA through the non-polar membrane of a cell to release the siRNA inside the cell.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, the terms "oligomerization" and "polymerization" are used interchangeably and refer to a polymerization reaction whereby two or more monomers are combined to produce an oligomer or polymer product. As used herein, the terms "oligomer" and "polymer" are used interchangeably. The term "co-oligomer" or "co-polymer" refers to an oligomer or polymer that includes 2 or more different monomer residues. An exemplary oligomerization reaction for producing co-oligomers of the disclosure is depicted in Scheme 1.

As used herein, the term "monomer" is used to refer to either the starting monomer reagent suitable for use in a oligomerization reaction, or to refer to one of the monomer units of an oligomer or polymer. As used herein, the term "sidechain" refers to the group of the monomer that branches from the backbone of a product co-oligomer.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule", "oligonucleotide" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), small interfering RNA (siRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡C—), isothiocyanato (—S—C≡N), azido (—N=$N^+$=$N^-$), formyl (—(CO)—H), thioformyl (—(CS)—H), amino (—$NH_2$), mono- and di-(C1-C24 alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), C1-C24 alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)$_n$-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Definitions of other terms and concepts appear throughout the detailed description below.

DETAILED DESCRIPTION OF THE EMBODIMENTS

As summarized above, co-oligomers, co-oligomer complexes and methods of using the same are provided, where the co-oligomer complexes a polyanion of interest, including without limitation a siRNA of interest, thereby increasing the transmembrane permeability of the polyanion. In some embodiments, the polyanion is a siRNA that targets expression of a protein implicated in a disease condition of interest, and complexing of the siRNA with the subject co-oligomer delivers an effective amount of the siRNA into a cell.

Also provided are pharmaceutical compositions that include the subject complexes, where the complex is formulated with a pharmaceutically acceptable excipient. Formulations may be provided in a unit dose, where the dose provides an amount of the compound effective to achieve a desired result, including without limitation inhibition of the expression of a protein target of a siRNA of interest.

These compounds and methods find use in a variety of applications in which delivery of siRNA into a cell is of interest.

Co-Oligomers

As summarized above, aspects of the disclosure include co-oligomers. In some embodiments, the co-oligomers include a first lipophilic monomer and a second hydrophilic monomer, and as such may be described as amphipathic. In some embodiments, the second hydrophilic monomer includes a positively charged group, e.g., a guanidinium group. The first and second monomers may be arranged in any convenient arrangement in the oligomer chain, e.g., as blocks or distributed randomly. The first lipophilic monomer has a hydrophobic sidechain. The second hydrophilic monomer includes a hydrophilic group in the sidechain (e.g., a guanidinium containing sidechain).

In some embodiments, the subject co-oligomer may further include one or more additional monomers. Any convenient monomers may be included in the subject co-oligomers to provide for one or more desirable properties, such as solubility, an optical property, a specific binding property or capability to protect siRNA from degradation. In some embodiments, the subject co-oligomers are biocompatible and/or biodegradable. For example, co-oligomers having a polycarbonate backbone would degrade slowly over time in vivo to produce non toxic fragments that would be eliminated. In some embodiments, the co-oligomers are non immunogenic.

The subject co-oligomer may include lipophilic and hydrophilic monomers, and at least one additional monomer. The arrangement of such monomers in the subject co-oligomer may be a random, block, or a mixture thereof. In such co-oligomers, the ratio of the monomers in the co-oligomer, and/or a block thereof, and the length of the co-oligomer may be selected to provide for a desirable property. For example, the subject co-oligomer may have include a sequence described by one of the following formulas: $(A)_{block}(B)_{block}(C)_{block}$; ABCD, BACD, CBDA, or other random sequence; ABCABCABC; $(A)_{block}(BCD)_{random}$; $(B)_{block}(ACD)_{random}$; where each A is independently a lipophilic monomer (e.g., a monomer having an alkyl or a cholesterol sidechain); each B is independently a hydrophilic monomer (e.g., a monomer having a guanidinium containing sidechain); and C and D are exemplary additional monomers.

Any convenient oligomerization chemistry may be used in preparing the subject co-oligomers, including but not limited to, cyclic carbonate ring-opening oligomerization chemistry, peptide chemistry, and carbohydrate chemistry. In some embodiments, the subject co-oligomers have a backbone where monomers are linked together via functional groups selected from the group consisting of an amide, a glycoside linkage, a carbonate, a carbamate, an ether, an ester, an amino linkage, phosphate, and mixtures thereof. In some embodiments, the subject co-oligomers have a backbone selected from a peptidic backbone, a polysaccharide, a dextran backbone, polyethylene glycol and polyethyleneimine. In some embodiments, the subject co-oligomers have a polycarbonate backbone. In some embodiments, the subject co-oligomer is a block co-polymer that includes one or more block of lipophilic monomers (e.g., monomers having a lipophilic sidechain as described herein) adjacent to one or more blocks of hydrophilic monomers (e.g., monomers having arginine containing sidechains).

The following are examples of co-oligomers of the disclosure and components for producing the same.

In some embodiments, the subject co-oligomer is described by formula (Ia) or formula (Ib):

(Ia)

(Ib)

where:
Y is hydrogen or an initiator group (e.g., ArCH$_2$X—, RCOX— or Ar—X—, where X is O, S or NH, Ar is an aryl (e.g., phenyl), and R is an alkyl or an aryl);
each A is independently a lipophilic monomer (e.g., a monomer having an alkyl or a cholesterol sidechain);
each B is independently a hydrophilic monomer (e.g., a monomer having a guanidinium containing sidechain);
x is an integer from 1 to 50; and
each m and each n is independently 0 or an integer from 1 to 30.

In some embodiments, in formula (Ia) or (Ib), x is 1, 2 or 3 (e.g., 1) and each $m_x$ and $n_x$ are independently an integer from 2 to 20 (e.g., 4 to 18, such as 4, 5, 6, 7, 8, 9, 10, 12, 14, 16, 17, or 18). In some embodiments, in formula (Ia) or (Ib), x is 1, $m_1$ is 4 and $n_1$ is 4. In some embodiments, in formula (Ia) or (Ib), x is 1, $m_1$ is 8 and $n_1$ is 9. In some embodiments, in formula (Ia) or (Ib), x is 1, $m_1$ is 17 and $n_1$ is 16.

In some embodiments, in formula (Ia) or (Ib), A and B form a polycarbonate backbone.

In some embodiments, in formula (Ia) or (Ib), the co-oligomer is a random co-oligomer of A and B monomers. In some embodiments, in formula (Ia) or (Ib), the co-oligomer is a block co-oligomer of A and B monomers (e.g., a diblock, a triblock, etc).

In some embodiments, the subject co-oligomer is described by the structure of formula (II):

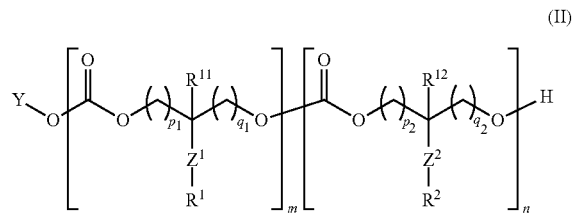
(II)

where:
Y is an initiator group;
p1 and q1 are each independently 0 or 1, where p1+q1≥1;
p2 and q2 are each independently 0 or 1, where p2+q2≥1;
each $Z^1$ and $Z^2$ is independently a linking group (e.g., a covalent bond, an ester, an amide, an ether, a thioether, a thioester, or a carbamate);
each $R^{11}$ and $R^{12}$ is independently selected from hydrogen and a lower alkyl (e.g., methyl);
m and n are each independently an integer from 1 to 30; and
each $R^1$ and $R^2$ is independently a sidechain group, where:
one of $R^1$ and $R^2$ is a lipophilic sidechain; and the other of $R^1$ and $R^2$ is -L-$Z^3$ where L is a linker and $Z^3$ is a hydrophilic group (e.g., a guanidinium, an imidazolyl, an ammonium (e.g., trimethylammonium), a phosphonium, a hydroxyl, or a polyethyleneglycol (PEG).

In some embodiments, in formula (II), Y is selected from PhCH$_2$X—, RCOX— and Ar—X—, where X is O, S or NH, and R is an alkyl or an aryl. In some embodiments, in formula (II), Y is PhCH$_2$O—.

In some embodiments, in formula (II), p1 and q1 are each 1. In some embodiments, in formula (II), either p1 is 1 and q1 is 0 or p1 is 0 and q1 is 1. In some embodiments, in formula (II), p2 and q2 are each 1. In some embodiments, in formula (II), either p2 is 1 and q2 is 0 or p2 is 0 and q2 is 1.

In some embodiments, in formula (II), each $Z^1$ and $Z^2$ is an ester linking group (—CO$_2$—).

In some embodiments, in formula (II), each $R^{11}$ and $R^{12}$ is methyl.

In some embodiments, in formula (II), each lipophilic sidechain is independently selected from a linear alkyl (e.g., methyl, ethyl, propyl, butyl, pentyl, hexyl, dodecyl), a branched alkyl (e.g., isopropyl, isobutyl, 3-hexyl), a cycloalkyl (e.g., cyclopropyl, cyclobutyl, cyclopentyl, cyclohexyl), an alkenyl, an alkynyl, a cholesterol, an aryl, an aralkyl (e.g., benzyl) or a heterocycle. In some embodiments, in formula (II), each lipophilic sidechain is dodecyl, hexyl, ethyl, or cholesterol.

In some embodiments, in formula (II), L is a $C_1$-$C_6$ linker (e.g., —$CH_2CH_2$—) and $Z^3$ is a guanidinium group. In some embodiments, $Z^3$ forms a pharmaceutically acceptable salt having a $X^-$ counterion. Any convenient counterions may be used, e.g., carbonates, phosphates, sulfates, chloride, TFA counteranion, sulphonates, phosphates, acetates or fatty acids (e.g., $CH_3(CH_2)_pCO_2^-$ where p is an integer from 1 to 30).

In some embodiments, in formula (II), each $R^1$ is a lipophilic sidechain and each $R^2$ is -L-$Z^3$. In some embodiments, in formula (II), each $R^1$ is -L-$Z^3$ and each $R^2$ is a lipophilic sidechain.

In some embodiments, in formula (II), m and n are each independently an integer selected from about 30 or less, about 25 or less, about 20 or less, about 18 or less, about 16 or less, about 14 or less, about 12 or less, about 10 or less, about 9 or less, about 8 or less about 7 or less, about 6 or less, about 5 or less, or about 4 or less. In some embodiments, in formula (I), m and n are each independently an integer from 2 to 20 (e.g., 3, 4, 5, 6, 7, 8, 9, 10, 12, 14, 16, 17 or 18). In some embodiments, for example, for siRNA, m and n are each 4. In some embodiments, m and n are each 7. In some embodiments, m is 8 and n is 9. In some embodiments, m and n are each 9. In some embodiments, m is 17 and n is 16. In some embodiments, m is 18 and n is 17.

In some embodiments, the ratio of monomers and the length of the subject co-oligomer may be selected depending on the size and charge of the polyanion of interest, and/or on the stoichiometry of the complex that is formed between the subject co-oligomer and polyanion.

In some embodiments, when the polydispersity of the subject co-oligomer is taken into account, the average m and n values may be used to describe the subject co-oligomer. In such cases, the average m and average n need not be integers as they represent average block sizes. In some embodiments, the average m is about 4.5 and the average n is about 5. In some embodiments, the average m and average n values may independently range from about 2.0 to about 20.0 (e.g., about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 12.0, about 14.0, about 16.0, about 17.0 or about 18.0).

In some embodiments, the subject co-oligomer is described by the structure of formula (III):

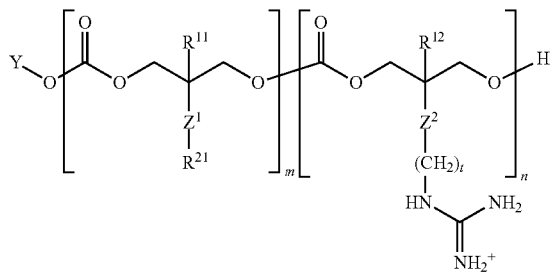

where:
Y, $R^{11}$, $R^{12}$, $Z^1$, $Z^2$, m and n are as defined above in formula (II);
$R^{21}$ is a lipophilic sidechain; and
t is an integer from 1 to 6 (e.g., 2).

In some embodiments, in formula (III), Y is selected from $PhCH_2X$—, RCOX— and Ar—X—, where X is O, S or NH, and R is an alkyl or an aryl. In some embodiments, in formula (III), Y is $PhCH_2O$—.

In some embodiments, in formula (III), each $Z^1$ and $Z^2$ is an ester linking group (—$CO_2$—), an amide linking group (e.g., —CONR— where R is H or and alkyl) or a thioester linking group (e.g., —C(=O)S—).

In some embodiments, in formula (III), each $R^{11}$ and $R^{12}$ is methyl.

In some embodiments, in formula (III), each $R^{21}$ is independently selected from a linear alkyl (e.g., methyl, ethyl, propyl, butyl, pentyl, hexyl, dodecyl), a branched alkyl (e.g., isopropyl, isobutyl, 3-hexyl), a cycloalkyl (e.g., cyclopropyl, cyclobutyl, cyclopentyl, cyclohexyl), an alkenyl, an alkynyl, a cholesterol, an aryl, an aralkyl (e.g., benzyl) or a heterocycle. In some embodiments, in formula (III), each $R^{21}$ is dodecyl, hexyl or ethyl.

In some embodiments, in formula (III), t is 2.

In some embodiments, in formula (III), m and n are each 4. In some embodiments, in formula (III), m and n are each 7. In some embodiments, m is 8 and n is 9. In some embodiments, in formula (III), m and n are each 9. In some embodiments, in formula (III), m is 17 and n is 16. In some embodiments, in formula (III), m is 18 and n is 17.

In some embodiments, the subject co-oligomer is described by the structure of formula (IV):

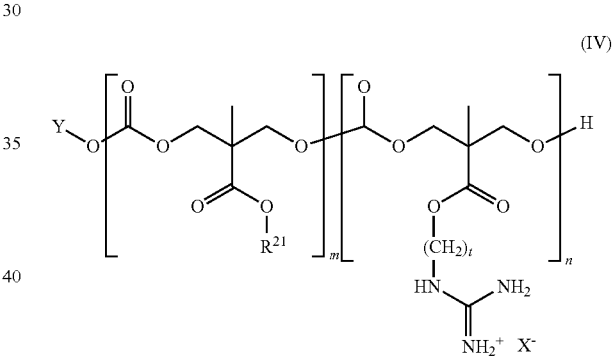

where:
Y, m, n, $R^{21}$ are as defined above in formula (III); and
$X^-$ is a counterion.

In some embodiments, in formula (IV), Y is $PhCH_2O$—.

In some embodiments, in formula (IV), each $R^{21}$ is dodecyl, hexyl or ethyl.

In some embodiments, in formula (IV), m and n are each 4. In some embodiments, in formula (IV), m and n are each 7. In some embodiments, in formula (IV), m is 8 and n is 9. In some embodiments, in formula (IV), m and n are each 9. In some embodiments, in formula (IV), m is 17 and n is 16. In some embodiments, in formula (IV), m is 18 and n is 17.

Any convenient arrangements of monomers can be used in the subject co-oligomers, for example, diblock co-oligomers, random co-oligomers containing two monomers, co-oligomers with three or blocks (triblock, etc.) or random co-oligomers with more different monomers (three, four or more monomers). For block co-oligomers, the order of initiation could be varied, e.g., according to the method of scheme 1. Such variations could produce exemplary arrangements of monomers in the subject co-oligomer as depicted below:

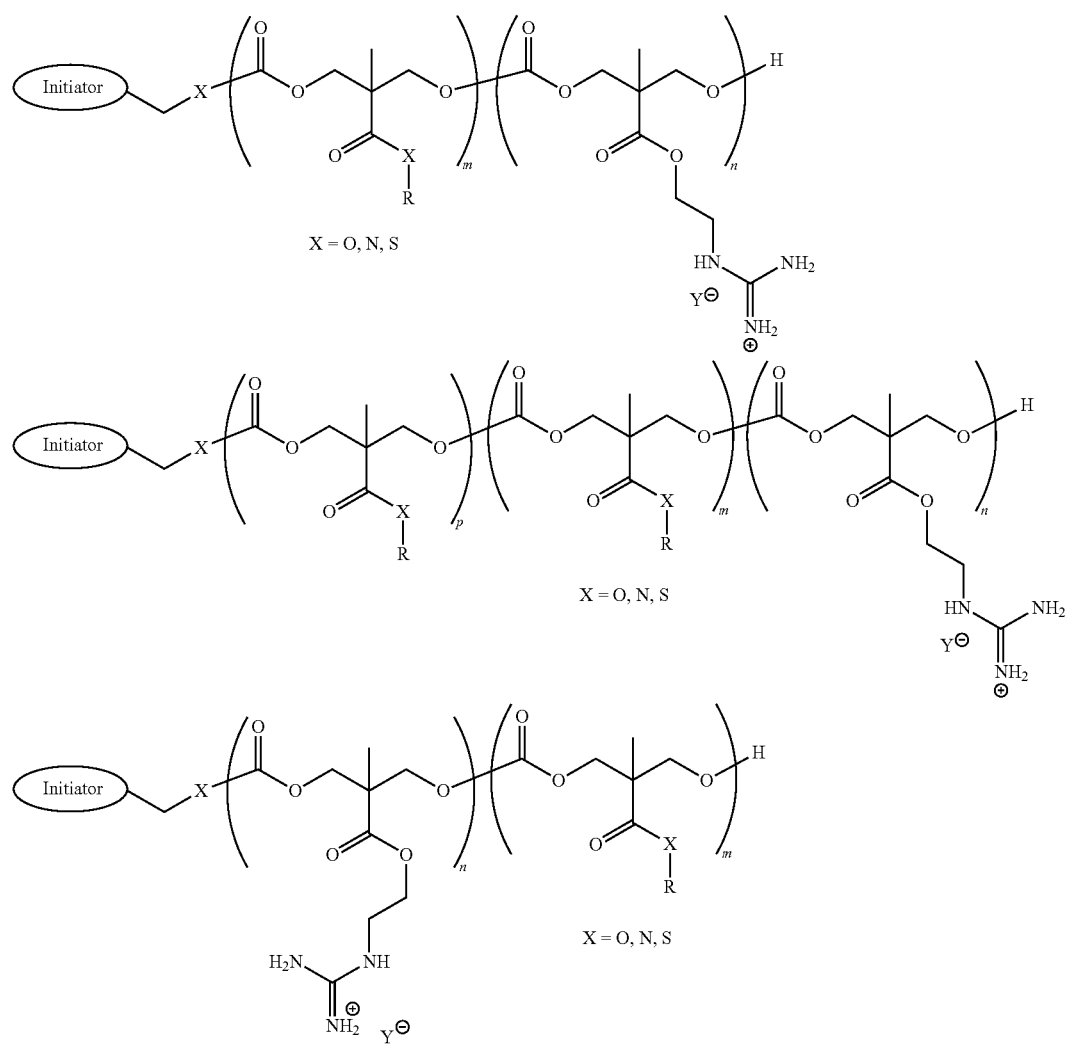
In some embodiments, the subject co-oligomer has a backbone that includes linking functional groups selected from amide, phosphate, carbamate, and mixtures thereof, e.g., a backbone as shown in one of the following structures:
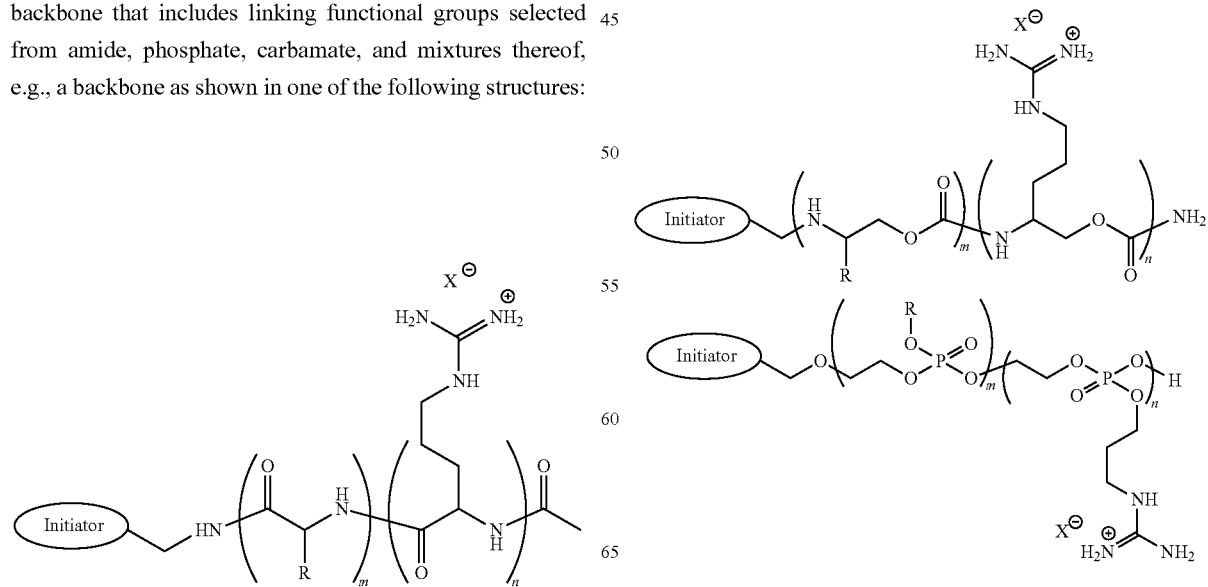

Length of Co-Oligomer

The length of the co-oligomer (i.e., the total number of monomers in the co-oligomer) may range from 2 to 100, such as from 4 to 50, 6 to 40, 6 to 35, 6 to 30, 6 to 25, 6 to 20, 6 to 18, 6 to 16, 6 to 14, 6 to 12, or 6 to 10. It is understood by one of ordinary skill in the art that depending on the chemistry used to prepare the co-oligomer, the co-oligomer may be polydisperse, e.g., the co-oligomer may be present as a mixture of oligomers having different lengths. In such cases, the length of the predominant species present in the mixture may be used to describe the co-oligomer. The co-oligomer may be further described by a polydispersity index (PDI=$M_w/M_n$), where $M_w$=the weight average molecular weight and $M_n$=the number average molecular weight. In some embodiments, the co-oligomer has a PDI of 2 or less, such as 1.9 or less, 1.8 or less, 1.7 or less, 1.6 or less, 1.5 or less, 1.4 or less, 1.3 or less, 1.2 or less, or 1.1 or less. Depending on the method of preparation the co-oligomer may also be a single compound.

In some embodiments, the length of the co-oligomer is about 40 or less, such as about 35 or less, about 30 or less, about 25 or less, about 20 or less, about 18 or less, about 16 or less, about 14 or less, about 12 or less, about 10 or less, about 9 or less, or about 8 or less. In some embodiments, the length of the co-oligomer is about 18 or less (e.g., about 16 or less, about 14 or less, about 12 or less, about 10 or less, such as 8), and has a PDI of 1.7 or less (e.g., 1.6 or less, 1.5 or less, 1.4 or less, 1.3 or less, 1.2 or less, or 1.1 or less).

Ratio of Lipophilic and Hydrophilic Monomers

The subject co-oligomers include at least a first lipophilic monomer and at least a second hydrophilic monomer. Additional types of lipophilic and/or hydrophilic monomers may be included. Exemplary lipophilic and hydrophilic monomers are described herein. Any convenient arrangement of the monomers along the backbone may be used. For example, the monomers may be arranged as one or more blocks of lipophilic monomers separated by one or more blocks of hydrophilic monomers. In such cases, each block may include a mixture of different lipophilic monomers, or a mixture of different hydrophilic monomers. Such co-oligomers may be referred to as block co-polymers (e.g., a diblock, a triblock, 4-block, 5-block, 6-block, etc) and may be described by the length of each block. For example, a diblock co-oligomer that includes one lipophilic block of length m and one hydrophilic block of length n may be referred to as a m:n diblock co-oligomer. In some embodiments, the co-oligomer is a 4:4, 5:5, 6:6, 7:7, 8:8, 9:9, 10:10, 8:9, 4:10, 10:4, 17:16, 18:17, 3:7, 4:7, 5:7, 6:7, or the like block co-oligomer. Each individual block of a co-oligomer may also be polydisperse, as described above.

The lengths of each monomer block may be selected to provide for a desirable property, such as cell permeability, affinity for siRNA, protection of siRNA or release of siRNA. In some embodiments, each block length is independently selected from about 30 or less, about 25 or less, about 20 or less, about 18 or less, about 16 or less, about 14 or less, about 12 or less, about 10 or less, about 9 or less, about 8 or less about 7 or less, about 6 or less, about 5 or less, or about 4 or less.

In some embodiments, the co-oligomer is a block co-oligomer that has lipophilic monomer block lengths of 8 or less (e.g., 8, 7, 6, 5 or 4) and hydrophilic monomer block lengths of 10 or less (e.g., 9, 8, 7, 6, 5 or 4). In some embodiments, the co-oligomer is a di-block.

Alternatively, the monomers may be arranged randomly. A random co-oligomer may include, 2 or more different monomers, such as 3 or more, or 4 or more different monomers arranged randomly is a sequence (e.g., a random arrangement including 2 or 3 different lipophilic monomers and one hydrophilic monomer).

The overall ratio of lipophilic to hydrophilic monomers may be selected to provide for a desirable property, such as cell permeability, or affinity for siRNA. In some embodiments, the ratio of lipophilic to hydrophilic monomers ranges from 0.4 to 2.5, such as 0.4 to 1.1 (e.g., 2:5, 3:7, 4:10, 8:9, 1:1, 18:17 or 17:16). In some embodiments, the ratio of lipophilic to hydrophilic monomers is about 0.9 to about 1.1 (e.g., 4.5:5, 8:9, 18:17). In some embodiments, two or more different co-oligomers may be combined in any convenient ratio of co-oligomers to bind to a polyanion of interest and provide for a desired property of the resulting complex.

Complexes

Also provided are compositions that include a complex of a subject co-oligomer and a polyanion of interest. Any convenient polyanion that includes multiple negatively charged groups can be complexed with the subject co-oligomers, including but not limited to, polynucleotides such as siRNA, modified siRNA, shRNA, DNA, aptamers, heparins, polysulfated carbohydrates and the like. In some embodiments, the hydrophilic sidechain groups (e.g., guanidinium groups) of a co-oligomer are capable of interacting electrostatically with the polyanionic backbone of a polynucleotide of interest (e.g., a siRNA) in the complex composition. In some embodiments, the ratio of polyanion to co-oligomer in the complex ranges from 1:1 to 1:100, such as 1:10 to 1:60 (e.g., 1:11, 1:30 or 1:52.5). The length, composition and stoichiometry of the subject co-oligomers in the complex may be selected to provide for a desired amount of electrostatic interactions with the polyanion of interest.

In some embodiments, the subject complex composition includes a siRNA molecule of interest. SiRNA based therapies have entered into clinical trials for a number of indications including cancer and viral infections, see e.g., Davidson, B. L. and McCray, P. B. "Current prospects for RNA interference-based therapies," Nature Reviews: Genetics 2011, 12, 329-340.

In some embodiments, the subject complex composition includes a mixture of two or more subject co-oligomers (e.g., where each of the two or more co-oligomers may be polydisperse) and a polyanion of interest (e.g., a siRNA).

Oliogmerization

The co-oligomers may be prepared using any convenient method, such as but not limited to an organocatalytic cyclic carbonate ring-opening oligomerization method as depicted in Scheme 1.

Scheme 1: Synthesis of co-oligomers

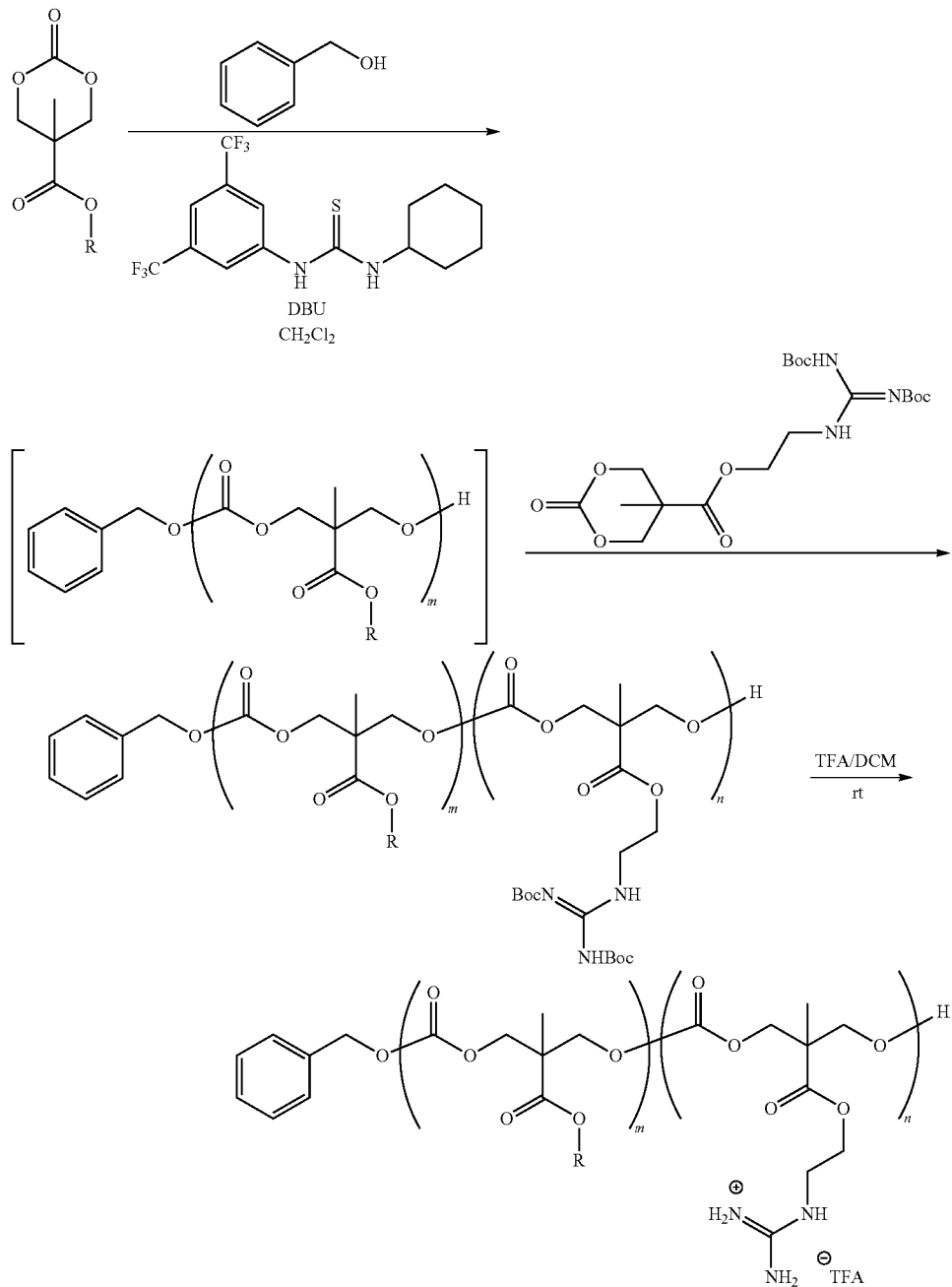

In some embodiments, the subject co-oligomers are block co-oligomers. Block co-polymers may be prepared according to a method as depicted in scheme 1 by including a first monomer in the reaction mixture with an initiator, and then adding a second monomer to the reaction mixture only after oligomerization has been initiated.

In some embodiments, the subject co-oligomers are random co-oligomers. Random co-oligomers may be prepared according to a method as depicted in scheme 1 by including both a first monomer and a second monomer in the reaction mixture with an initiator at the start of oligomerization.

Initiators

The subject co-oligomer may include an initiator group that derives from an initiator reagent of the oligomerization reaction. The initiator reagent is a compound that is capable of initiating the oligomerization reaction to produce a co-polymer. In general terms, the initiator provides a functional group that reacts with a monomer to produce an intermediate that reacts with further monomers in an oligomerization reaction.

In some embodiments, the oligomerization reaction may be facilitated by the inclusion of an additional reagent (e.g., a deprotecting agent, a catalyst, a base, an acid, or irradiation of light) that may act by unmasking the initiator or by catalyzing the oligomerization. For example, in the oligomerization reaction depicted in scheme 1, a thiourea catalyst and DBU base is included in the reaction mixture in addition to the benzyl alcohol initiator.

Any convenient initiator may be used in the preparation of the subject co-oligomers. In some embodiments, the initiator is selected from ArCH$_2$XH, RCOX— and Ar—X—, where Ar is an aryl group (e.g., phenyl), X is O, S or NH, and R is an alkyl or an aryl. For example, the initiator may be selected from benzyl alcohol, phenol, aniline, thiophenol, and benzoic acid or other carboxylic acid. In some embodiments, the initiator may further include one or more additional functional groups, such as functionality for targeting (e.g., a specific binding moiety), detection (e.g., a chromophore, fluorophore, or the like), to improve a pharmacokinetic property (e.g., polyethylene glycol (PEG) or cholesterol), to aid in packaging of the polyanion of interest, to aid in stability of the complex, to assist in release of the polyanion, to provide a second oligomerization initiating group, or to allow for post-polymerization attachment of a desired moiety. In some embodiments, the initiator can provide for visualization of uptake or release of a siRNA and could be used for diagnostics. In some embodiments, the initiator is a bifunctional initiator that includes two oligomerization initiating groups, e.g., an initiator that can initiate oligomerization from multiple sites. Exemplary initiators are shown below:

Initiator =

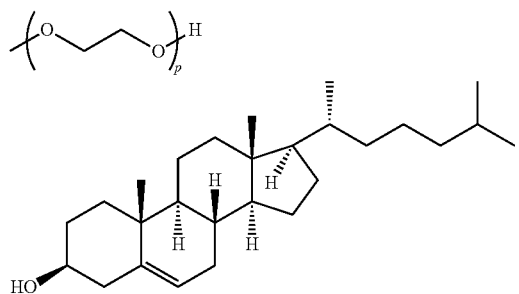

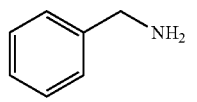

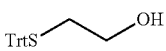

For post-polymerization attachment of a desired functionality through a disulfide bond

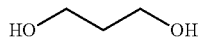

In some embodiments, the initiator includes a functional group suitable for use in post-oligomerization modification of the co-oligomer, where the functional group may be optionally protected with a protecting group. Exemplary functional groups suitable for use in post-oligomerization modifications include those described by Hermanson, G. T. in "Bioconjugate Techniques", second Ed., Academic Press, London, 2008. In some embodiments, the initiator includes one or more groups selected from a thiol, an azido, an alkyne, an active ester (e.g., a N-hydroxysuccinimide), an amino, a hydroxyl, an aldehyde, a hydrazide, a carboxylic acid, and protected derivatives thereof.

Monomers

Any suitable monomers may be used in the subject co-oligomers. In some embodiments, the subject co-oligomers include a first lipophilic monomer that has a lipophilic sidechain and a second hydrophilic monomer that includes a hydrophilic sidechain group (e.g., a guanidinium, an ammonium, an imidiazolyl or a phosphonium).

In some embodiments, the lipophilic monomer includes a lipophilic sidechain, such as but not limited to, an alkyl (e.g., a lower alkyl or a longer aliphatic alkyl chain), an aromatic group such as an aryl or a heterocycle, an unsaturated aliphatic group, an alkynyl, an alkenyl, an aralkyl (e.g., benzyl), etc. Some exemplary monomers are depicted below:

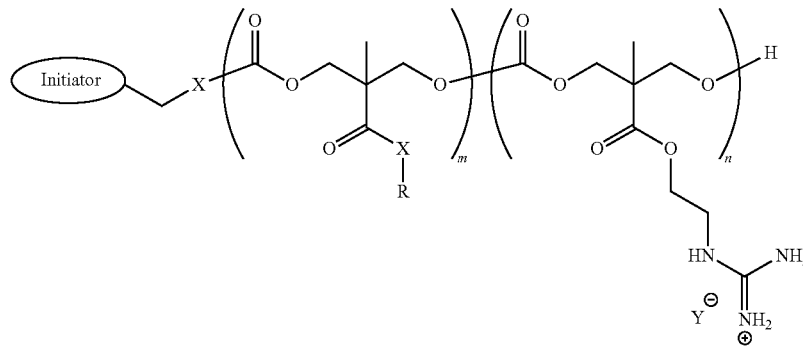

X = O, N, S

R = 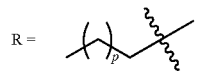 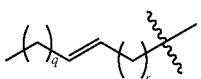 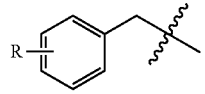 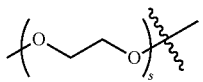

p = 2-4, 6-10, >11 where q, r, s are each independently an integer from 1 to 100, such as 1 to 59, or 1 to 20 (e.g., 2-4, 6-10 or 11, or 45 or more; and the phenyl ring may be optionally substituted with a substituent (R).

In some embodiments, the hydrophilic monomer includes a guanidinium group. In some embodiments, the hydrophilic monomer is a monomer as described by Cooley et al., "Oligocarbonate Molecular Transporters," U.S. Pat. No. 7,939,621, the disclosure of which is herein incorporated by reference in its entirety.

Methods

The present disclosure provides methods of delivery of a polyanion into a cell by complexing the polyanion with a subject co-oligomer, thereby protecting it from degradation, increasing the ability of the polyanion to permeate into the cell and allowing for its release after cell entry. The subject methods also provide a broad platform for delivery of a siRNA molecules of interest into a cell by complexing with the subject co-oligomer.

Polyanions of interest are described herein, including but not limited to siRNA, modified siRNA, DNA, aptamers, heparins, sulfated carbohydrates, polycarboxylates and the like. In some embodiments, the subject method is a method of delivering a siRNA molecule of interest into a cell, where the cell includes a target of the siRNA. SiRNAs of interest include those described in Davidson, B. L. and McCray, P. B. "Current prospects for RNA interference-based therapies," Nature Reviews: Genetics 2011, 12, 329-340, the disclosure of which is herein incorporated by reference in its entirety.

In practicing methods of the disclosure, the cells of interest may be contacted with the effective amount of the subject complex in an in vitro or ex vivo culture system, or in vivo. For example, a subject complex may be contacted to primary cells grown under standard tissue culture conditions or alternatively to cells that are part of a whole animal (e.g., administered to a subject). As such, the target cell or collection of cells may vary, where the collection of cells may be cultured cells, a whole animal or portion thereof, e.g., tissue, organ, etc. As such, the target cell(s) may be a host animal or portion thereof, or may be a therapeutic cell (or cells) which is to be introduced into a multi-cellular organism, e.g., a cell employed in gene therapy. In such methods, an effective amount of an subject complex is administered to the target cell or cells, e.g., by contacting the cells with the complex, by administering the complex formulation to the animal, etc. By effective amount is meant a dosage sufficient to modulate expression of a target protein of the subject complex in the target cell(s), as desired.

In the subject methods, the subject complex may be contacted with the target cells using any convenient protocol that results in the desired knockdown of protein target expression.

In some embodiments, the subject method is a method of treating a subject for a disease. In some embodiments, the subject method includes administering to the subject an effective amount of a complex composition that includes the subject co-oligomer (e.g., as described above) and a polyanion (e.g., siRNA) of interest. In some embodiments, the disease condition is treated by reducing the expression of a protein target of a siRNA of interest. In some embodiments, the subject is human. In some embodiments, the subject complex is administered as a pharmaceutical preparation.

In some embodiments, the subject co-oligomer delivers siRNA into a cell, as determined by a dual fluorescent assay, e.g., by an assay that determines the reduction of expression of a fluorescent protein target after treatment with a co-oligomer/siRNA complex, relative to a fluorescent control protein, by measuring the fluorecence of the protein target relative to the control. In certain embodiments, application of the subject complex reduces expression of the protein target by 50% or more, such as 60% or more, 70% or more, 80% or more, 90% or more, 95% or more, or 99% or more.

In certain embodiments, the subject co-oligomers have no significant effect on the viability of a mammalian cell, as determined by a cell cytotoxicity assay, e.g., as determined by administering a subject co-oligomer and the subject co-oligomer/siRNA complex to a immortalized human keratinocyte (HaCaT) cell and determining the number of viable cells present. The subject co-oligomers may exhibit a % cell viability, as compared to a control (e.g., a PBS control), of 15% or more, such as 20% or more, 30% or more, 40% or more, 50% or more, 60% or more, 70% or more, 80% or more, 90% or more, 100% or more, 120% or more, or even higher. The subject co-oligomers may exhibit a $EC_{50}$ value of 1 nm or higher, such as 100 nm or higher, 300 nm or higher, 1 um or higher, 3 um or higher, 10 um or higher, or even higher.

The protocols that may be employed in determining the activity of the subject complexes are numerous, and include but are not limited to cell-free assays, e.g., binding assays; protein expression assays; mRNA quantification assays, e.g., reverse transcription-quantitative polymerase chain reaction (RT-qPCR) assays; cellular assays in which a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject co-oligomer or complex that includes a siRNA of interest. In certain embodiments, the sample is suspected of containing the protein target of a siRNA of interest and the subject method further comprises evaluating whether the subject complex inhibits the expression of the target.

In certain embodiments, the subject co-oligomer is a modified compound that includes a label, e.g., a fluorescent label, and the subject method further includes detecting the label, if present, in the sample, e.g., using optical detection. In certain embodiments, the subject complex includes a labelled siRNA.

In another embodiment of the subject method, the sample is known to contain the target of a siRNA of interest.

In certain embodiments, the subject co-oligomer is a modified compound that includes a label, and the method further includes detecting the label in the subject. Alternatively the subject complex includes a labelled siRNA. The selection of the label depends on the means of detection. Any convenient labeling and detection systems may be used in the subject methods, see e.g., Baker, "The whole picture," Nature, 463, 2010, p977-980. In certain embodiments, the complex includes a fluorescent label suitable for optical detection. In certain embodiments, the complex includes a radiolabel for detection using positron emission tomography (PET) or single photon emission computed tomography (SPECT). In some cases, the complex includes a paramagnetic label suitable for tomographic detection. The subject complex may be labeled, as described above, although in some methods, the complex is unlabelled and a secondary labeling agent is used for imaging.

Pharmaceutical Compositions

The above-discussed co-oligomer complexes can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject co-oligomer complexes are formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In some cases, the formulation is stored at about 4° C. In some cases, the formulation is stored at −20° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, the subject co-oligomer and an siRNA agent, e.g., an siRNA described by Davidson, B. L. and McCray, P. B. "Current prospects for RNA interference-based therapies," Nature Reviews: Genetics 2011, 12, 329-340 are administered to individuals in a formulation as a complex with a pharmaceutically acceptable excipient(s). The subject complexes, as well as additional therapeutic agents as described herein for combination therapies, can be administered orally, subcutaneously, intramuscularly, parenterally, by inhalation or other routes. The subject complexes and additional therapeutic agents may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject complexes may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

A therapeutically effective amount of the subject complex is an amount that is effective to reduce the expression of a protein target of a polyanion of interest (e.g., a siRNA) by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%, compared to the level of expression in an untreated individual, or to a placebo-treated individual. Those skilled in the art can readily measure the expression of such protein targets, using standard assay methods, many of which are commercially available, and are used routinely in clinical settings. Methods of measuring protein expression include immunological-based methods, e.g., enzyme-linked immunosorbent assays (ELISA), radioimmunoassays, and the like, using antibody specific for a given protein. Those skilled in the art know the normal ranges for such serum proteins.

A therapeutically effective amount of a compound in this context can be regarded as an amount that is effective in reducing the incidence (e.g., the likelihood that an individual will develop) of a disorder associated with the protein target by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with the subject complex is effective in reducing the incidence of a disorder associated with the protein target can readily be determined by those skilled in the art.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is number average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1

Synthesis of Co-Oligomers

The co-oligomers were constructed using an organocatalytic cyclic carbonate ring-opening oligomerization strategy as shown in the following scheme 1.

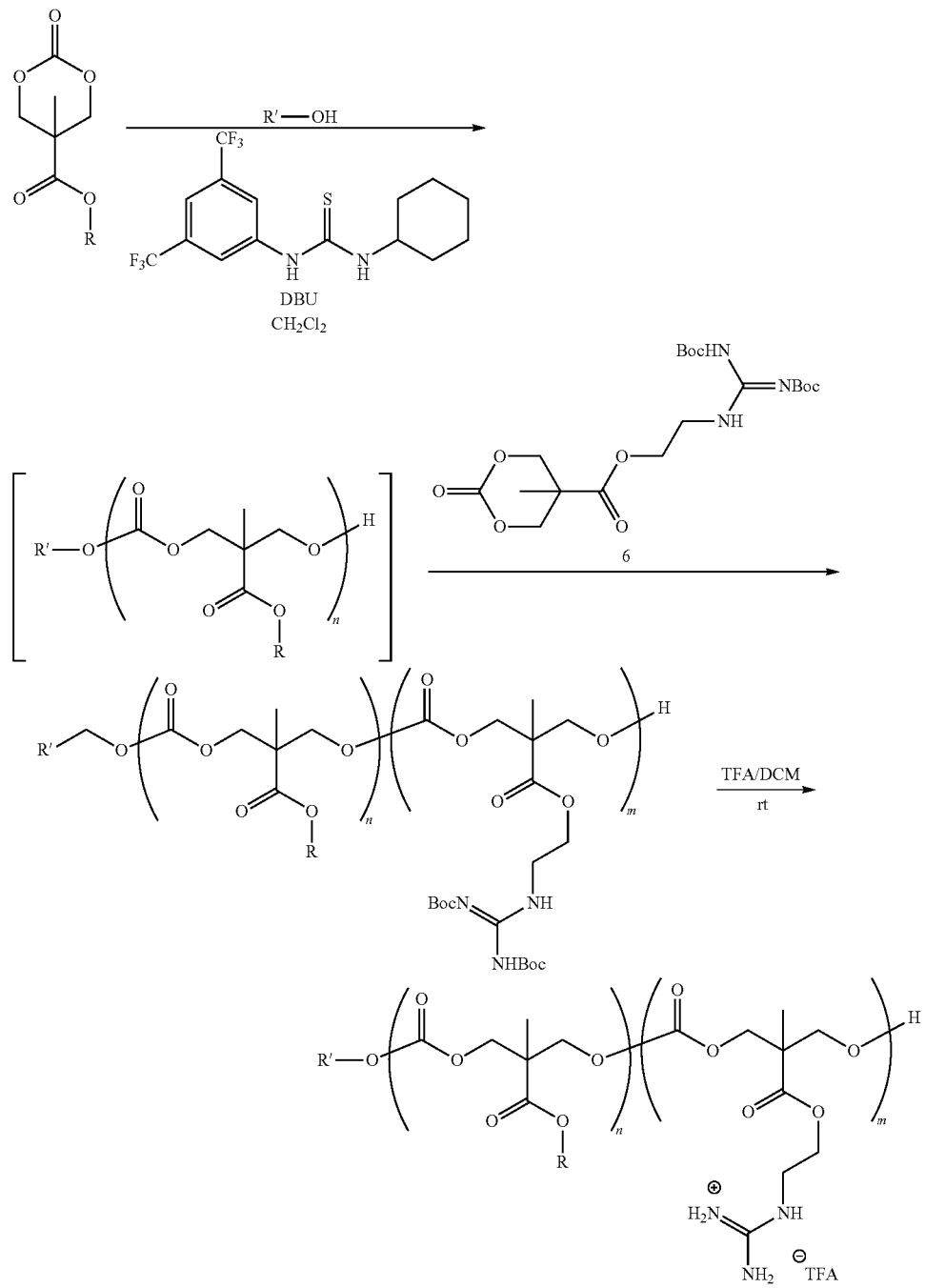

Scheme 1: Synthesis of co-oligomers

-continued

R' = 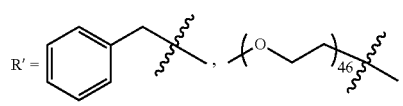

More specifically, In a glove box with N₂ atmosphere thiourea catalyst (5 mol % with respect to monomer), DBU (5 mol % with respect to monomer), and benzyl alcohol or poly(ethylene glycol) methyl ether (1 equivalent) were charged in a glass vial equipped with a stir bar. In a separate reaction vessel was added lipid monomer (m equivalents, for random oligomers also added guanidinium monomer at this point). To both reaction vessels was added $CH_2Cl_2$ (to total 1.323 g/mol between the two reaction vessels), then the solution containing the lipid monomer was added to the solution containing the catalyst in one portion via pipette. The reaction was stirred at rt in the glovebox for 1.25 hours. In a separate vessel was weighed guanidinium monomer (n equivalents, for random oligomers this was done in the previous step), and this monomer was added as a solid to the reaction mixture. The mixture was stirred at rt in the glovebox for 1.25 hours, then a small amount of benzoic acid was added to quench the catalyst. The crude reaction solution was transferred into a dialysis bag (1,000 g/mol cut off), and the solution dialyzed against MeOH for 24 hours, the MeOH solution was changed after 6 hours. The remaining solvent was evaporated yielding the co-oligomer as a clear waxy solid. Degree of polymerization was determined by NMR end group analysis and polydispersity index was determined by gel permeation chromatography (GPC).

The co-oligomers were then deprotected in the following manner: to a solution of co-oligomer in $CH_2Cl_2$ (4.5 mL) was added TFA (0.50 mL). The reaction vessel was sealed and stirred at rt for 14 hours then the solvent concentrated under reduced pressure. Additional $CH_2Cl_2$ was added and the solution was further concentrated in vacuo to yield the deprotected amphipathic carbonate co-oligomers as clear oils (quantitative yield). Full deprotection was confirmed by NMR analysis.

The synthesis shown in the scheme above provides block co-oligomers. If both monomer types are added at the start of the reaction (as described in the procedure above) then random co-oligomers are produced. By varying the properties of the monomers and the initiator used, the relative ratios of the monomers used, and the overall length of the co-oligomers, the physical properties and performance of the co-oligomers are tuned. Benzyl alcohol or polyethylene glycol were used as the initiator.

The following co-monomers for co-oligomerization with the guanidinium monomer (Scheme 1) were used to prepare co-oligomers according to the method of scheme 1:

Ethyl: 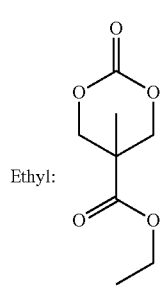

Hexyl: 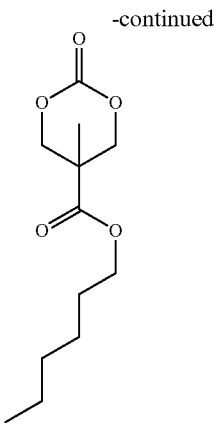

Dodecyl: 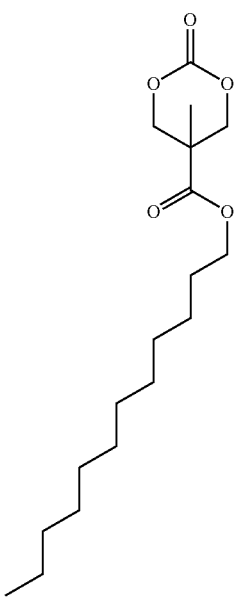

Branched Hexyl: 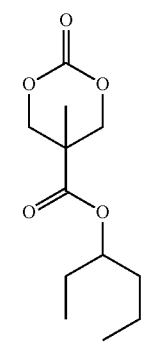

-continued

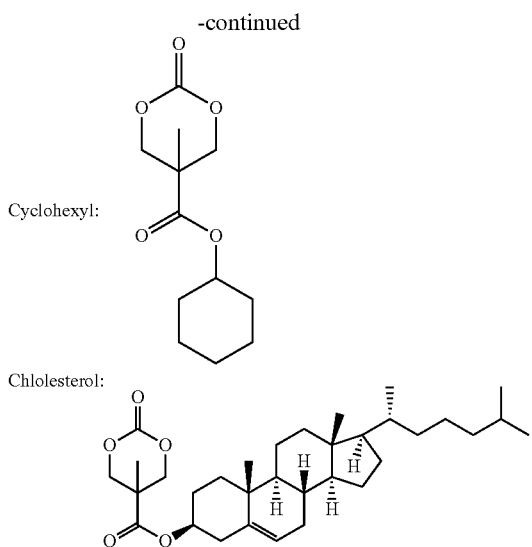

Exemplary co-oligomers synthesized by the synthetic scheme are shown in Table 1.

TABLE 1

Exemplary co-oligomers prepared according to scheme 1. Co-oligomers are block unless otherwise noted.

| Name | m | n | R | Initiator | Polydispersity (PDI) |
|---|---|---|---|---|---|
| DP8 | 0 | 8 | — | Benzyl | 1.183 |
| H:G 4:4 | 4 | 4 | Hexyl | Benzyl | 1.461 |
| H:G 8:9 | 8 | 9 | Hexyl | Benzyl | 1.325 |
| Random H:G 9:9 | 9 | 9 | Hexyl | Benzyl | 1.262 |
| H:G 4:10 | 4 | 10 | Hexyl | Benzyl | 1.154 |
| H:G 10:4 | 10 | 4 | Hexyl | Benzyl | 1.199 |
| H:G 17:16 | 17 | 16 | Hexyl | Benzyl | 1.353 |
| E:G 5:5 | 5 | 5 | Ethyl | Benzyl | 1.461 |
| E:G 8:9 | 8 | 9 | Ethyl | Benzyl | 1.303 |
| E:G 19:19 | 19 | 19 | Ethyl | Benzyl | 1.420 |
| D:G 4:4 | 4 | 4 | Dodecyl | Benzyl | 1.609 |
| D:G 4.5:5 | 4.5 | 5 | Dodecyl | Benzyl | 1.333 |
| Random D:G 4:4 | 4 | 4 | Dodecyl | Benzyl | 1.373 |
| PEG-D:G 2.5:3 | 2.5 | 3 | Dodecyl | PEG2000 | 1.314 |
| D:G 7:7 | 7 | 7 | Dodecyl | Benzyl | 1.472 |
| D:G 18:17 | 18 | 17 | Dodecyl | Benzyl | 1.472 |
| Chol:G 3:7 | 3 | 7 | Cholesterol | Benzyl | 1.380 |
| cycloH:G 8:8 | 8 | 8 | Cyclohexyl | Benzyl | 1.428 |

Example 2

Preparation of siRNA Complexes and Functional Assay

To form a siRNA/co-oligomer complex, a solution of a synthesized and deprotected co-oligomer is mixed with a solution of siRNA at a desired ratio of co-oligomer to siRNA. This simple mixing spontaneously forms particles (as determined by dynamic light scattering and gel electrophoresis). Complexes can also be formed by mixing solutions of two or more distinct co-oligomers with one another, and then mixing with a solution of siRNA. More specifically, In some cases, using gel electrophoresis, siRNA/co-oligomer complexes have been shown to degrade within 24 hours at 37° C. in phosphate buffered saline (PBS, pH=7.4), and the degraded components shown to have no cytotoxicty by an MTT assay.

Delivery of functional siRNA into a cell was confirmed by first incubating cells with the siRNA/co-oligomer complexes, then observing selective knockdown of a protein target in a cell with a dual fluorescence assay in immortalized human keratinocytes (HaCaT) cells. In this assay, a siRNA entitled "CBL3" targets a td-tomato protein, and the percent expression of this protein is measured relative to an enhanced GPF (eGFP) control protein. More specifically, The tdTomato/EGFP expressing HaCaT cells were plated 20,000 cells/well in a 24-well plate and allowed to incubate at 37° C. for 18-24 hours. siRNA:co-oligomer solutions were made by mixing RNAse free PBS pH 7.4 (104-111 μL), various amount of co-oligomer from a 1.25 mM stock solution (4-10 μL in RNAse free PBS), and 10 μL CBL3 (or scrambled siRNA) siRNA (25 μM stock in RNAse free PBS pH 7.4) to achieve various siRNA:co-oligomer ratios (generally 4.77/1+/−, 125 μL total volume). The complexes were allowed to form at rt over 30 minutes. The Lipofectamine controls were prepared in Optimem according to the manufacturer's instructions. For siRNA alone, 1.95 μL 150 μM CBL3 siRNA was added to 300 μL serum-free DMEM media. The cells were then washed with ~1.0 mL serum-free DMEM media, then 750 μL serum-free DMEM media was added to the cells alone wells, 675 μL to the siRNA alone or Lipofectamine 2000 wells, or 712.5 μL was added to all siRNA:co-oligomer wells. Finally, 75 μL of siRNA alone or siRNA:Lipofectamine was added to the appropriate wells, and 37.5 μL of the siRNA:co-oligomer complexes in PBS were added to each well, all conditions in triplicate. The cells were allowed to incubate with the compounds for 4 hours at 37° C., then the media was removed and replaced with 1.0 mL of fresh, serum-containing DMEM media. After an additional 65-72 hours of incubation, the cells were washed with 1.0 mL PBS, 0.4 mL trpysin-EDTA was added, and the cells were incubated for 15 minutes at 37° C. (gently shaken after 10 minutes). Next, 0.6 mL of serum-containing DMEM media was added and each well was transferred to a 15 mL centrifuge tube and centrifuged (1200 rpm for 5 minutes). The media over each pellet was removed by aspiration, then the pellet was re-dispersed in PBS (0.250 mL), transferred to FACS tubes, and read on a flow cytometry analyzer. All cells collected were gated for positive EGFP expression. The data presented are the mean fluorescent signals from 10,000 cells analyzed. The mean fluorescent signal for td-tomato and EGFP was determined. This value of td-tomato expression/EGFP expression Is then compared to the td-tomato/EGFP value for untreated cells to obtain a percent expression.

Figure 2:
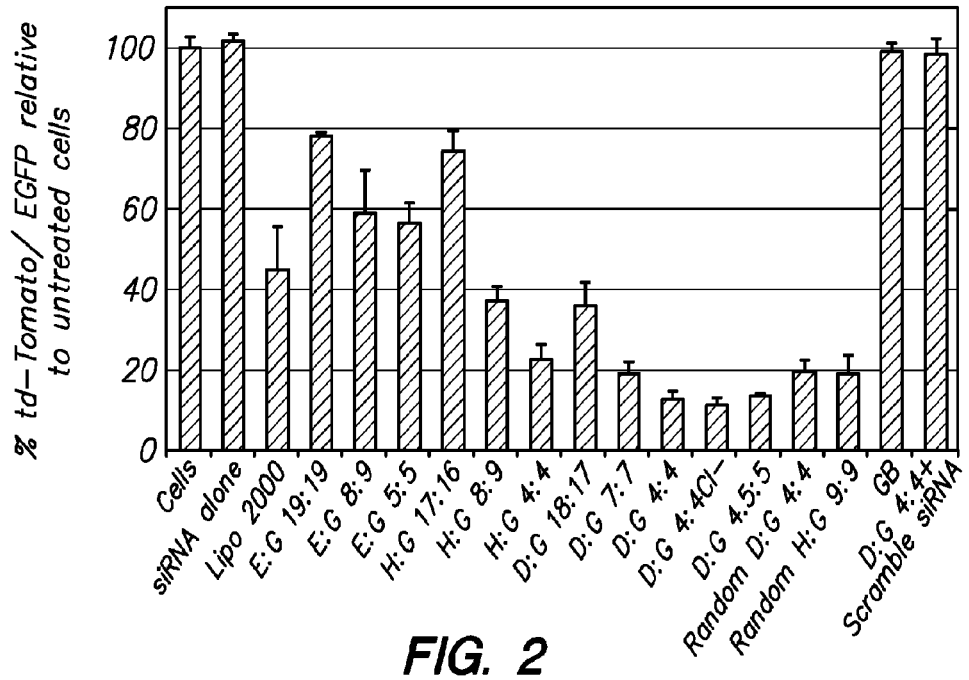
FIG. 2 illustrates the knockdown of a target protein, and a dose dependence of knockdown, using exemplary siRNA/co-oligomer complexes.
Figure 3:
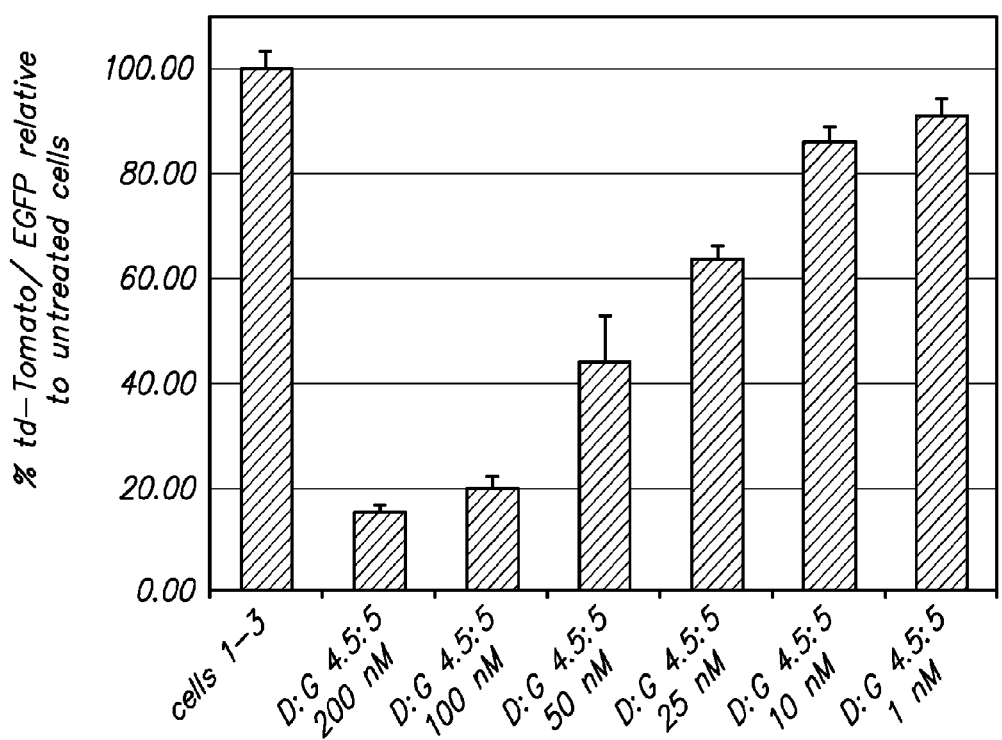
FIG. 3 illustrates the knockdown of a target protein, and a dose dependence of knockdown, using exemplary siRNA/co-oligomer complexes.

Values obtained for several of the co-oligomers are shown in the graph below. Up to ~90% knockdown of the desired protein target was achieved, and several co-oligomers outperformed Lipofectamine2000 (a common commercial transfection agent) at the same concentration of siRNA (in the instance below, 100 nM with respect to siRNA). Controls show that if the siRNA is applied to cells without formulation with the co-oligomer, no knockdown is achieved, and that application to cells of a complex with a scrambled siRNA and co-oligomer does not result in protein knockdown. Additionally, oligomers of guanidinium alone do not show any uptake of siRNA. Knockdown of the target protein occurs in a dose dependent manner using these siRNA/co-oligomer complexes (see FIGS. 2 and 3).

Figure 4:
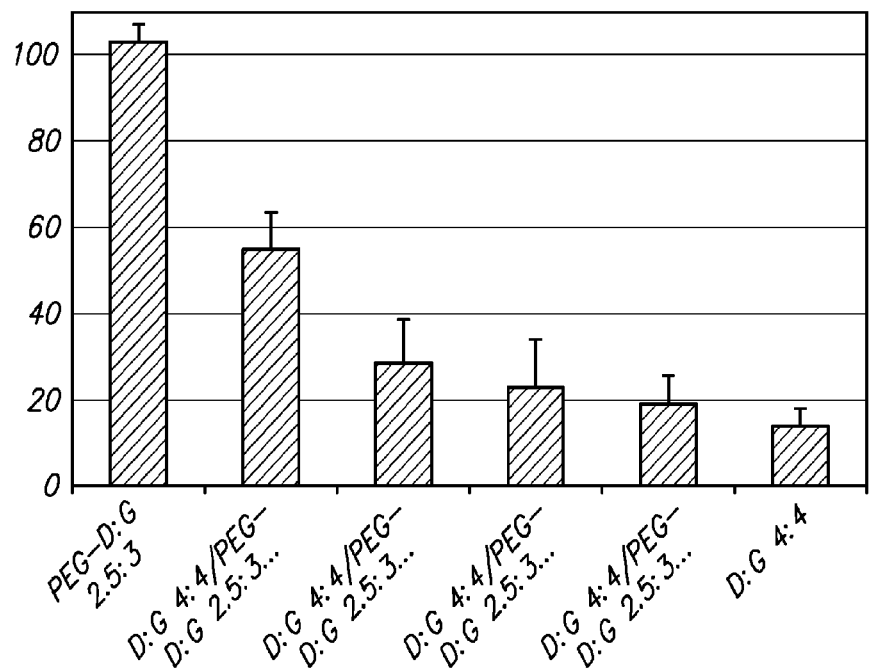
FIG. 4. Knock-down with complexes from PEG-initiated co-oligomers mixed with a dodecyl-containing co-oligomer (D:G 4:4) at varying molar ratios and then with siRNA.
Figure 5:
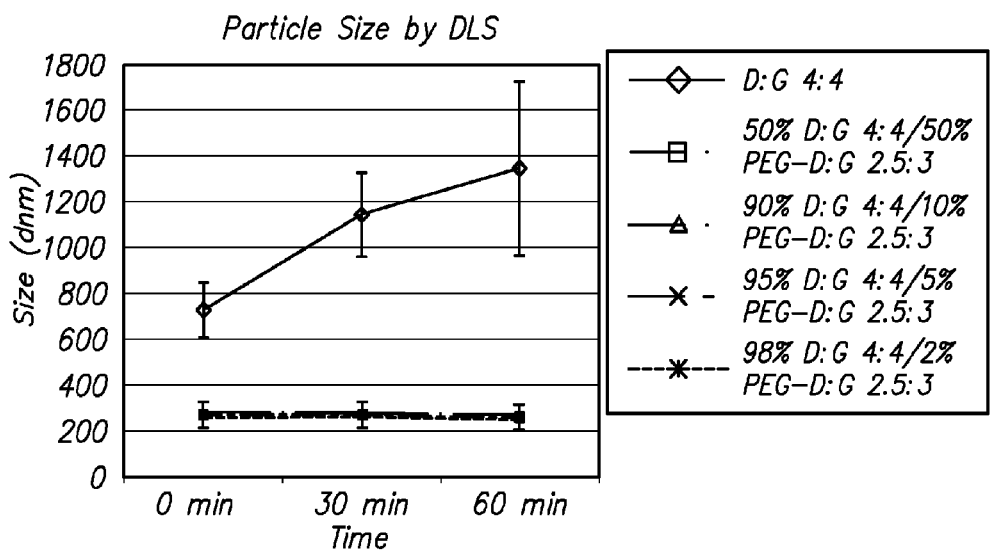
FIG. 5. Size as determined by DLS of complexes from PEG-initiated co-oligomers mixed with a dodecyl-containing co-oligomer (D:G 4:4) at varying molar ratios and then with siRNA.

In addition, it was shown that two distinct co-oligomers could be mixed together at varying molar percentages before being mixed with siRNA to form complexes, and that these mixtures had interesting or unique properties beyond that of each co-oligomer alone. For example, when PEG-initiated co-oligomers are mixed with a dodecyl-containing co-oligomer (D:G 4:4) at varying molar ratios and then with siRNA, the resulting complexes have the knockdown shown in FIG. 4 and the size properties (as determined by DLS) shown in FIG. 5.

Figure 6:
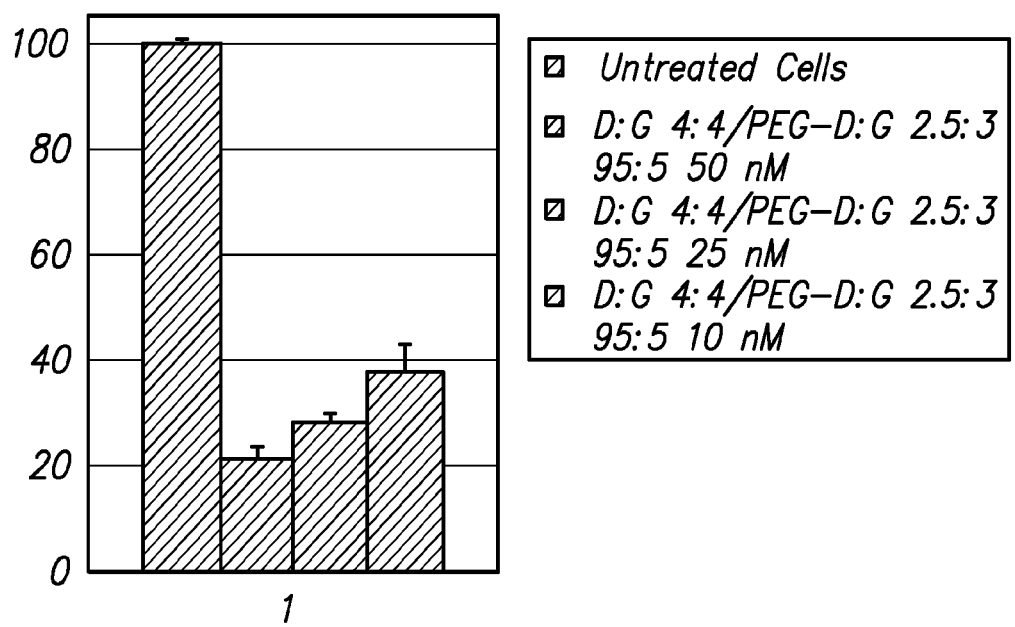
FIG. 6. Knock-down with complexes from PEG-initiated co-oligomers containing an siRNA that targets the tdTomato protein (CBL3 siRNA).

These siRNA:co-oligomer complexes have also shown efficacy in primary keratinocytes. Dual reporter primary keratinocytes expressing both tdTomato and EGFP were treated with siRNA/co-oligomer complexes containing an siRNA that targets the tdTomato protein (CBL3 siRNA) and the knockdown analyzed by flow cytometry. The results of this knockdown with complexes composed of mixtures of PEG-D:G 2.5:3 and D:G 4:4 are shown in FIG. 6, with the complexes demonstrating up to ~80%.

This ability of the siRNA/co-oligomer complexes to deliver siRNA into a cell was also confirmed by observation of fluorescent protein knockdown by fluorescence microscopy, where significant reduction in td-tomato (red signal) could be directly observed in cells treated with siRNA/co-oligomer complex. In addition, entry of FITC-tagged siRNA formulated as a FITC-siRNA/co-oligomer complex into cells was also observed by fluorescence microscopy. In addition, when using a siRNA against the keratin protein K6a in HaCaT cells, the siRNA/co-oligomer complexes reduced levels of mRNA of K6a relative to a control (GAPDH), as determined by a reverse transcription—quantitative polymerase chain reaction (RT-qPCR) assay. The siRNA/co-oligomer complexes have also been shown to deliver siRNA to and subsequently reduce mRNA levels of a target protein in an OVCAR cell line.

What is claimed is:

1. A composition comprising:
   a siRNA; and
   a co-oligomer having a length of 40 monomers or less that is a random co-oligomer or a block co-oligomer of lipophilic monomers and hydrophilic monomers, wherein the co-oligomer is described by formula (I):

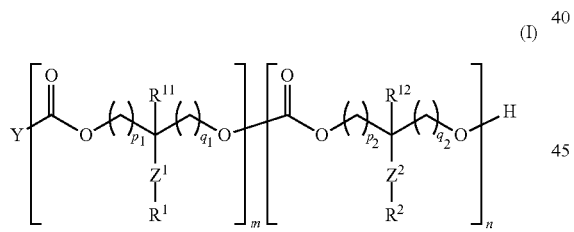

(I)

wherein:
   Y is an initiator group;
   p1 and q1 are each independently 0 or 1, where p1+q1≥1;
   p2 and q2 are each independently 0 or 1, where p2+q2≥1;
   each $Z^1$ and $Z^2$ is independently a linking group;
   each and $R^{11}$ and $R^{12}$ is independently selected from hydrogen and a lower alkyl;
   m and n represent a number of lipophilic or hydrophilic monomers in the random or block co-oligomer and are independently an integer from 1 to 30, wherein the sum of m and n is 40 monomers or less; and
   each $R^1$ and $R^2$ is independently a sidechain group, wherein:
   one of $R^1$ and $R^2$ is a lipophilic sidechain of the lipophilic monomers; and
   the other of $R^1$ and $R^2$ is -L-$Z^3$ where L is a linker and $Z^3$ is a hydrophilic positively charged group of the hydrophilic monomers.

2. The composition of claim 1, wherein Y is selected from $PhCH_2X$—, RCOX— and Ar—X—, wherein X is O, S or NH, and R is an alkyl or an aryl.

3. The composition of claim 1, wherein p1 and q1 are each 1.

4. The composition of claim 1, wherein either p1 is 1 and q1 is 0 or p1 is 0 and q1 is 1.

5. The composition of claim 1, wherein p2 and q2 are each 1.

6. The composition of claim 1, wherein either p2 is 1 and q2 is 0 or p2 is 0 and q2 is 1.

7. The composition of claim 1, wherein each $Z^1$ and $Z^2$ is an ester linking group (—$CO_2$—).

8. The composition of claim 1, wherein each $R^{11}$ and $R^{12}$ is methyl.

9. The composition of claim 1, wherein each lipophilic sidechain is independently a linear alkyl having from 7 to 24 carbon atoms, or a branched alkyl having from 7 to 24 carbon atoms.

10. The composition of claim 1, wherein each lipophilic sidechain is dodecyl.

11. The composition of claim 1, wherein L is a $C_1$-$C_6$ linker and $Z^3$ is a guanidinium group.

12. The composition of claim 1, wherein each $R^1$ is a lipophilic sidechain and each $R^2$ is -L-$Z^3$.

13. The composition of claim 1, wherein each $R^1$ is -L-$Z^3$ and each $R^2$ is a lipophilic sidechain.

14. The composition of claim 1, wherein the co-oligomer is a random co-oligomer of lipophilic and hydrophilic monomers having a length of about 20 or less.

15. The composition of claim 14, wherein the ratio of lipophilic to hydrophilic monomers ranges from 0.4 to 2.5.

16. The composition of claim 1, wherein the co-oligomer comprises a block of 8 or less lipophilic monomers adjacent to a block of 10 or less hydrophilic monomers, wherein the co-oligomer is described by formula (III):

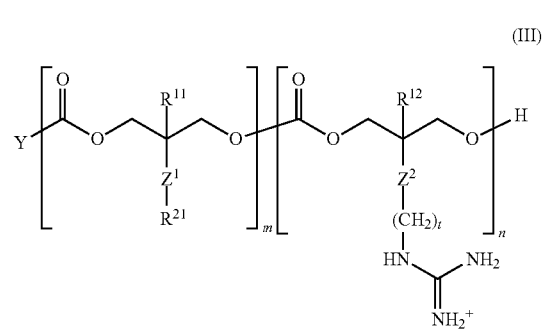

(III)

wherein:
   m is 8 or less;
   n is 10 or less;
   $R^{21}$ is the lipophilic sidechain; and
   t is an integer from 1 to 6.

17. The composition of claim 16, wherein Y is selected from $PhCH_2X$—, RCOX— and Ar—X—, where X is O, S or NH, and R is an alkyl or an aryl.

18. The composition of claim 16, wherein each $Z^1$ and $Z^2$ is an ester linking group (—$CO_2$—), an amide linking group (—CONR—) where R is H or an alkyl, or a thioester linking group (—C(=O)S—).

19. The composition of claim 16, wherein each and $R^{11}$ and $R^{12}$ is methyl.

20. The composition of claim 16, wherein each $R^{21}$ is independently a linear alkyl having from 7 to 24 carbon atoms, or a branched alkyl having from 7 to 24 carbon atoms.

21. The composition of claim 16, wherein each $R^{21}$ is dodecyl.

22. The composition of claim 16, wherein t is 2.

23. The composition of claim 16, wherein m and n are each independently 5 or less.

24. The composition of claim 16, wherein the co-oligomer is described by formula (IV):

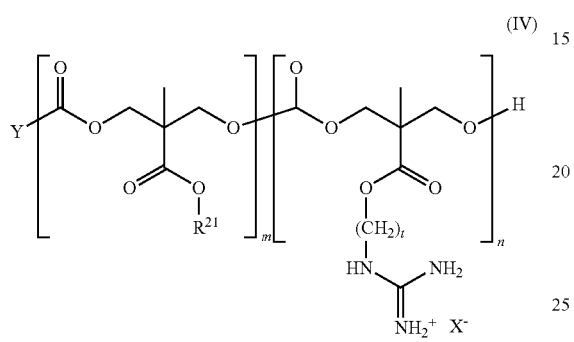

wherein:
m is 8 or less;
n is 10 or less;
t is an integer from 1 to 6; and
$X^-$ is a counterion.

25. The composition of claim 24, wherein Y is $PhCH_2O—$.

26. The composition of claim 24, wherein each $R^{21}$ is dodecyl, or hexyl.

27. The composition of claim 24, wherein m and n are each independently 5 or less.

28. A pharmaceutical composition comprising the composition of claim 1 and a pharmaceutically acceptable excipient.

29. A method for intracellular delivery of a siRNA to a cell, the method comprising:
complexing the siRNA with a co-oligomer having a length of 40 monomers or less that is a random co-oligomer or a block co-oligomer of lipophilic and hydrophilic monomers, wherein the co-oligomer is described by formula (I):

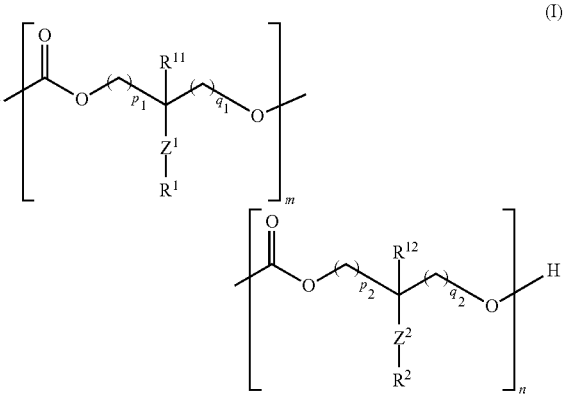

wherein:
Y is an initiator group;
p1 and q1 are each independently 0 or 1, where p1+q1≥1;
p2 and q2 are each independently 0 or 1, where p2+q2≥1;
each $Z^1$ and $Z^2$ is independently a linking group;
each and $R^{11}$ and $R^{12}$ is independently selected from hydrogen and a lower alkyl;
m and n represent a number of lipophilic or hydrophilic monomers in the random or block co-oligomer and are each independently an integer from 1 to 30, wherein the sum of m and n is 40 monomers or less; and
each $R^1$ and $R^2$ is independently a sidechain group, wherein:
one of $R^1$ and $R^2$ is a lipophilic sidechain of the lipophilic monomers; and
the other of $R^1$ and $R^2$ is $-L-Z^3$ where L is a linker and $Z^3$ is a hydrophilic positively charged group of the hydrophilic monomers;
to produce a siRNA / co-oligomer complex; and
contacting the cell with the complex.

30. A method for inhibiting the expression of a target protein in a cell, the method comprising contacting the cell with an effective amount of the composition of claim 1.

31. The method of claim 30, wherein the target protein is a target of the siRNA of the composition.

32. A method of treating a subject for a disease condition, the method comprising administering to the subject an effective amount of the composition of claim 1;
to treat the subject for the disease condition.

33. The method of claim 32, wherein the disease condition results from the expression of a protein target of the siRNA of the composition.

* * * * *